(12) United States Patent
Owusu et al.

(10) Patent No.: US 6,306,381 B1
(45) Date of Patent: Oct. 23, 2001

(54) METHOD AND COMPOSITION FOR TREATING *PSEUDOFOLLICULITIS BARBAE*

(76) Inventors: Yaw A. Owusu, 3400 Gallant Fox Trail, Tallahassee, FL (US) 32308; Edward J. Pye, 3206 N. Ridge Rd., Tall, FL (US) 32310

(*) Notice: Subject to any disclaimer, the term of this patent is extended or adjusted under 35 U.S.C. 154(b) by 0 days.

(21) Appl. No.: 09/519,194

(22) Filed: Mar. 6, 2000

(51) Int. Cl.[7] .................................................. A61K 7/15
(52) U.S. Cl. ........................... 424/73; 424/401; 424/74
(58) Field of Search ............................ 424/73, 74, 401; 514/886, 887, 848

(56) References Cited

U.S. PATENT DOCUMENTS

| | | | |
|---|---|---|---|
| 4,867,967 | * 9/1989 | Crutcher | 424/73 |
| 5,435,997 | * 7/1995 | Burns | 424/73 |
| 5,494,669 | * 2/1996 | Bailey | 424/195.1 |

FOREIGN PATENT DOCUMENTS

357034186A * 2/1982 (JP).

* cited by examiner

*Primary Examiner*—Thurman K. Page
*Assistant Examiner*—Liliana Di Nola-Baron
(74) *Attorney, Agent, or Firm*—John Wiley Horton

(57) ABSTRACT

A composition for conditioning the skin and for treating pseudofolliculitis barbae. Also disclosed is a method for making said composition. The composition is comprised of water, Aloe Vera juice, ammonium alum, glycerine, and ethanol. It can be made using relatively unsophisticated processing equipment. The process essentially comprises adding Aloe Vera juice to water, heating the water almost to its boiling point, adding glycerine and ammonium alum, allowing the mixture to cool, and adding a small amount of ethanol to avoid precipitation of the ammonium alum during prolonged storage.

8 Claims, 1 Drawing Sheet

METHOD AND COMPOSITION FOR TREATING *PSEUDOFOLLICULITIS BARBAE*

BACKGROUND

1. Field of Invention

This invention relates to the field of skin lotions, such as aftershave lotions. More specifically, the invention comprises a composition particularly suited to alleviating the occurrence of pseudofolliculitis barbae. Also disclosed is a method for making the composition.

2. Description of Prior Art

Shaving the facial skin is a common practice for most men. For those men having tightly curled facial hair, however, shaving can cause a recurring and significant problem. When sheared, a tightly coiled hair follicle will tend to grow by curving backward toward the skin. Over the course of a single day's growth, the tip of the follicle may actually be pressing back into the skin. Since the razor leaves a sharp sheared edge on the follicle tip, the hair may actually penetrate the skin and continue proceeding inward. This condition is commonly known as an "ingrown hair."

The epidermis (skin) reacts to the invading hair follicle as it would any other foreign object. The result is a swollen bump in the region. Secondary bacterial infection often results. Full blown pseudofolliculitis barbae ("PFB") is typically characterized by irritating bumps, itchiness, and discoloration of the affected areas. PFB becomes part of an accelerating cycle. The bumps are present the next time shaving takes place, resulting in a cut of the raised area and further irritation.

While present in all racial groups, PFB is particularly common in Black men. Published studies show that the condition affects over 80% of the Black male population. The only way to break the cycle is to cease shaving—an impractical alternative for most men.

Several prior art patents have addressed the treatment of PFB. U.S. Pat. No. 4,867,967 to Crutcher (1989) discloses a method of treating PFB. It specifies a composition including water, xanthum gum, aloe vera powder-200, alum, allantoin, glycerol, propylene glycol, and povidone-iodine. Several different mixture ratios are disclosed. The critical ingredient is the povidone-iodine.

U.S. Pat. No. 5,747,021 to McKenzie et.al. (1998) likewise discloses a composition intended to treat PFB. This invention comprises a homopolymer of acrylic acid combined with numerous other ingredients. A complex process for making the composition is disclosed. Unfortunately, the process and composition disclosed in McKenzie require the use of sophisticated process equipment. The McKenzie patent also fails to disclose a styptic agent, which would certainly be advantageous in the treatment of existing PFB—owing to the frequent cuts caused by shaving the bumps.

U.S. Pat. No. 5,914,103 to Armbruster et.al. (1999) discloses a shaving lotion particularly suited for use with an electric razor. While not specifying PFB in the disclosure, the invention does discuss "razor rash." The specification discloses a composition of 20 ingredients, many of which are fairly complex chemical formulations. Again, the disclosed composition requires the use of sophisticated process equipment. Like the McKenzie disclosure, Armbruster et.al. also fails to include a styptic agent to stop blood flow from razor cuts.

U.S. Pat. No. 4,463,016 to Burgess (1984) discloses a PFB treatment composition featuring a complex compound based on a Benzene ring. The Burgess disclosure lists several formulations with twelve other ingredients in addition to the Benzene ring based compound.

U.S. Pat. No. 5,494,669 to Bailey (1996) discloses a topical solution comprising alophatic alcohol, liquid aloe, liquid camphor, and the soluble portions of fig leaves. It does claim to be effective against PFB. It does not appear to disclose a styptic agent.

U.S. Pat. No. 5,853,709 to Willis et.al. (1998) discloses an after shave composition particularly suited to the treatment of PFB. This disclosure does feature a styptic agent, along with several other ingredients. One disclosed composition includes 21 ingredients. Many of these are complex formulation, again requiring the use of sophisticated lab equipment.

As stated previously, PFB is most prevalent among the Black population. The Black population is concentrated in many areas of the world where sophisticated lab equipment and processing facilities are not available. The prior art compositions and methods are therefore limited in that they:

1. Do not include an agent for stemming blood flow from shaving cuts;
2. Require the use of complex chemical ingredients which may be unavailable in many parts of the world;
3. Require the use of complex laboratory and processing equipment which may be unavailable in many parts of the world; and
4. Are relatively expensive to produce, owing to the complexity of the processes and ingredients.

OBJECTS AND ADVANTAGES

Accordingly, several objects and advantages of the present invention are:

1. To provide ingredients for skin conditioning, control of blood flow, and the treatment of PFB;
2. To provide a composition which can be made from relatively simple and easily obtained ingredients;
3. To provide a composition which may be produced without the necessity for complex laboratory and processing equipment; and
4. To provide a composition which is relatively inexpensive.

SUMMARY OF THE INVENTION

The present invention comprises an after shave composition which is particularly suited for the treatment of PFB-type bumps. It is formulated using materials that may be obtained in relatively undeveloped regions of the world. It can be made without the use of expensive chemical process equipment.

The manufacturing process starts with the leaves of the Aloe Vera plant. The succulent tissue inside the Aloe Vera leaves is removed and placed in a volume of water. The water and Aloe Vera product is agitated constantly for about ten minutes. Next, the mixture is filtered to remove solid materials. The resulting filtrate is then placed in a vessel suitable for heating. The filtrate is then heated to near 100 degrees Celsius. While the temperature remains elevated, quantities of glycerine and ammonium alum are added. The mixture is constantly agitated while the new ingredients are added.

The mixture is then allowed to cool to room temperature. The resulting product is effective as an aftershave for the treatment of PFB. Unfortunately, however, the product has a relatively short shelf life. A white gelatinous precipitate will form in the mixture in as little as six days. This precipitate results in an unappealing appearance for the product. While the precipitate can be filtered out, it consists primarily of the ammonium alum. Thus, filtering out the precipitate would remove one of the product's primary active ingredient. It was therefore desirable to prevent the precipitation from occurring.

The inventors have determined that the addition of a relatively small amount of ethanol during the manufacturing process prevents the formation of precipitates in the product. The ethanol has added antiseptic properties for the aftershave. It is not, however, sufficiently concentrated to produce an unpleasant stinging sensation when applied.

DETAILED DESCRIPTION OF THE INVENTION

Figure 1:
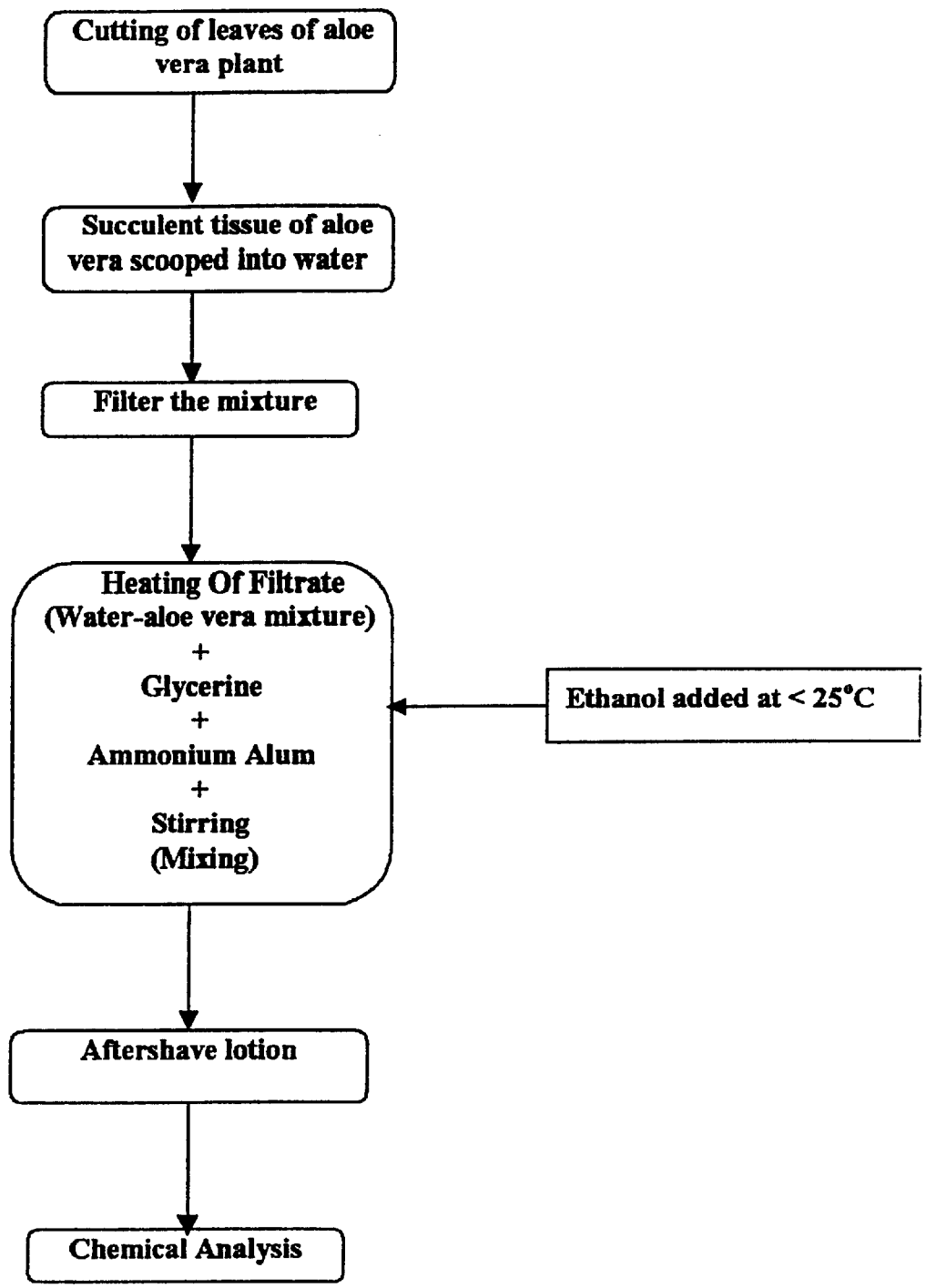
FIG. 1 describes the process employed to make the composition of the invention.

Shaving lotions are commonly composed of several ingredients, each with a different intended effect. The ingredients for the present invention were chosen both for their intended effect and their widespread availability. Ammonium alum (ammonium aluminum sulfate) was chosen to act as a skin softening agent. It also produces a pronounced stringent effect, meaning that it causes the skin to tighten and thereby make the facial hairs stand straight up.

Glycerine (1,2,3-propanetriol, glycerine) was included for its ability to soften the beard by acting as a wetting agent—thereby making the facial hair easier to cut. It also provides some lubrication value for the mechanical shearing action of the razor against the skin. The interior pulp of the Aloe Vera plant was included for its ability to cure cuts. It also provides a moisturizing and lubrication value.

The process employed to make the composition is as follows: The leaves of the Aloe Vera plant are cut. The succulent tissue within the leaves is scooped out and placed in water. Approximately six mature Aloe Vera leaves are added to approximately 1 gallon of clear tap water (purified water being unnecessary). The mixture is stirred continuously for about ten minutes in order to allow the water to extract most of the juicy liquid within the Aloe Vera pulp.

The mixture is then filtered using filter paper. The filtration process can be accelerated by using a suction pump, though this is not strictly necessary. The filtrate is then transferred to a vessel suitable for heating.

The filtrate is then heated to the boiling point of the water and held there. The heating should be done in a covered or sealed vessel in order to minimize the loss of water mass. While the heating continues, a quantity of glycerine is added. Next, a quantity of ammonium alum is added. The mixture is continuously stirred during the addition process.

Mixing continues for at least two minutes after adding the glycerine and ammonium alum. The heat source is then removed and the mixture is allowed to cool slowly. Stirring is continued for approximately five minutes after removing the heat, after which time the mixture is left stagnant.

As explained previously, if the mixture is bottled and stored at this point, a white gelatinous precipitate will be formed in a matter of several days. In order to avoid this problem, it is necessary to add a small amount of ethanol to the mixture. The mixture is allowed to cool to near room temperature (approximately 25 degrees Celsius). At this point, the ethanol is added and mixed in. It would be possible to add the ethanol earlier in the process, but a significant portion of the ethanol would be lost to evaporation. Thus, it is advantageous to wait until the prior ingredients cool to near room temperature.

The addition of the small amount of ethanol extends the products shelf life indefinitely. No precipitates were formed in seven weeks of testing this mixture. The process described is illustrated in flow chait form in FIG. 1.

It is desirable to minimize the quantity of ethanol employed. A high percentage causes an unpleasant stinging sensation when applied to the face. Thus, it is important to determine the minimum percentage of ethanol required to stabilize the product.

EXAMPLE I

Example I comprises the original formulation prior to the addition of any alcohol. It consists of the following ingredients:

| Ingredients | Weight (grams) | % Weight |
| --- | --- | --- |
| clear tap water | 946.25 | 93.54 |
| ammonium alum | 28.25 | 2.79 |
| glycerine | 37.17 | 3.67 |

This formulation was prepared according to the process described previously, except that the Aloe Vera leaves were omitted in order to simplify the early results. A white gelatinous precipitate started to form in this formulation after seventeen days.

EXAMPLE II

Straining the white precipitate out of the composition resulted in a significant reduction in the amount of measured ammonium alum. The ammonium alum thus became the suspected cause of the precipitation problems. Accordingly, a series of experiments was conducted in which the percentage weight of the ammonium alum was reduced. This alteration resulted in the following composition:

| Ingredients | Weight (grams) | % Weight |
| --- | --- | --- |
| clear tap water | 946.25 | 97.75 |
| ammonium alum | 9.42 | 0.97 |
| glycerine | 12.39 | 1.28 |

This second composition formed a white gelatinous precipitate in thirty-five days. Thus, reducing the concentration of ammonium alum did improve the situation. Unfortunately, the reduction in ammonium alum concentration reduced the effectiveness of the composition as a shaving lotion.

EXAMPLE III

The prior examples did not include the Aloe Vera extract, which was originally considered one of the desired ingredients. The Aloe Vera was added in Example III, which had the following composition:

| Ingredients | Weight (grams) | % Weight |
| --- | --- | --- |
| clear tap water + aloe | 946.25 | 93.54 |
| ammonium alum | 28.25 | 2.79 |
| glycerine | 37.17 | 3.67 |

This third composition formed a white gelatinous precipitate after only six days, with the addition of the Aloe Vera exacerbating the earlier problem.

EXAMPLE IV

A new formulation was created, again reducing the amount of ammonium alum. The objective was to determine if the addition of the aloe vera juice was actually making the precipitation problem worse. This fourth formulation had the following composition:

| Ingredients | Weight (grams) | % Weight |
| --- | --- | --- |
| clear tap water + aloe | 946.25 | 97.75 |
| ammonium alum | 9.42 | 0.97 |
| glycerine | 12.39 | 1.28 |

This formulation produced the same white precipitate after only six days. At this point a separate experiment was performed in an attempt to conclusively determine whether the ammonium alum was responsible for the precipitation problem. Two separate formulations were made—one containing only water and glycerine, and the other containing only water and ammonium alum.

No precipitation formed in the water/glycerine mixture during a six week period. In contrast, precipitate stated forming in the water/ammonium alum mixture in only six days. Since, ammonium alum was considered critical to the utility of the finished product, another ingredient was required to stop the precipitation.

EXAMPLE V

A new formulation was created, using the original concentration of ammonium alum, but adding ethanol as described previously. The fifth formulation had the following composition:

| Ingredients | Weight (grams) | % Weight |
| --- | --- | --- |
| clear tap water + aloe | 946.25 | 85.12 |
| ammonium alum | 28.25 | 2.54 |
| glycerine | 37.17 | 3.34 |
| ethanol | 100.00 | 9.00 |

No precipitate formed in this formulation after seven weeks. The ethanol was thus proved effective in eliminating the precipitation problem. However, the concentration of ethanol used in Example V produces a stinging sensation when applied to the face. It also tends to dry the skin. Thus, a reduction in the ethanol content was desired.

EXAMPLE VI

A new formulation was created having the following composition:

| Ingredients | Weight (grams) | % Weight |
| --- | --- | --- |
| clear tap water + aloe | 946.25 | 87.08 |
| ammonium alum | 28.25 | 2.60 |
| glycerine | 37.17 | 3.42 |
| ethanol | 75.00 | 6.90 |

The formulation of Example VI also failed to form a precipitate in seven weeks.

EXAMPLE VII

A new formulation was created to further reduce the ethanol concentration:

| Ingredients | Weight (grams) | % Weight |
| --- | --- | --- |
| clear tap water + aloe | 946.25 | 89.13 |
| ammonium alum | 28.25 | 2.66 |
| glycerine | 37.17 | 3.50 |
| ethanol | 50.00 | 4.71 |

The formulation of Example VII formed no precipitate in seven weeks. In testing, the formulation of Example VII was found very pleasant, without a noticeable stinging sensation. Thus, Example VII is the preferred embodiment of the present invention.

The preferred embodiment has a pH between 3.40 and 3.45. It has a specific gravity between 1.01 and 1.02. It has an indefinite shelf life, provided that it is stored in appropriate sealed containers. The applicants have also discovered that methanol can be substituted for ethanol in the formulations presented above.

SUMMARY, RAMIFICATIONS AND SCOPE

Accordingly, the reader will appreciate that the present invention provides an effective treatment for pseudofolliculitis barbae which can be produced using readily available materials. The invention has additional advantages in that it:

1. Provides ingredients for skin conditioning and control of blood flow from cuts;
2. Provides a composition which can be made using a relatively simple process; and
3. Provides a composition which is relatively inexpensive.

Although the preceding description contains significant detail, it should not be construed as limiting the scope of the invention but rather as providing illustrations of the preferred embodiment of the invention. Many variations could be made in the formulations presented without affecting the novel aspects of the invention. Thus, the scope of the invention should be fixed by the following claims, rather than by the examples given.

Having described our invention, we claim:

1. A topical agent for treating pseudofolliculitis barbae and conditioning the skin, consisting essentially of:
   a. Aloe Vera mixed in a volume of water, wherein the weight of said Aloe Vera and said water combined is in the range of from about 85% to about 90% of the total weight of said topical agent;
   b. glycerine, wherein the weight of said glycerine is in the range of from about 2% to about 5% of the total weight of said topical agent;
   c. ammonium alum, wherein the weight of said ammonium alum is in the range of from about 2% to about 5% of the total weight of said topical agent, and;

d. ethanol, wherein the weight of said ethanol is in the range of from about 4% to about 9% of the total weight of said topical agent.

2. The topical agent of claim 1, wherein said Aloe Vera comprises the juice extracted from the leaves of an Aloe Vera plant.

3. A topical agent for treating pseudofolliculitis barbae and conditioning the skin, consisting essentially of:
   a. Aloe Vera mixed in a volume of water, wherein the weight of said Aloe Vera and said water combined is in the range of from about 85% to about 90% of the total weight of said topical agent;
   b. glycerine, wherein the weight of said glycerine is in the range of from about 2% to about 5% of the total weight of said topical agent;
   c. ammonium alum, wherein the weight of said ammonium alum is in the range of from about 2% to about 5% of the total weight of said topical agent, and;
   d. methanol, wherein the weight of said ethanol is in the range of from about 4% to about 9% of the total weight of said topical agent.

4. A process for creating a topical agent for treating pseudofolliculitis barbae and conditioning the skin, comprising:
   a. adding Aloe Vera juice to a volume of water to form a mixture;
   b. heating said mixture of (a) to near the boiling point of said water;
   c. adding glycerine and ammonium alum to said mixture of (a) to form a second mixture;
   d. allowing said mixture of (c) to cool to near room temperature; and
   e. Adding ethanol to said mixture of (d), in order to prevent precipitation in said mixture of (d).

5. A method for treating pseudofolliculitis barbae comprising applying the topical agent of claim 1 to the affected area of the skin.

6. A method for treating pseudofollculitis barbae comprising applying the topical agent of claim 2 to the affected area of the skin.

7. A method for treating pseudofolliculitis barbae comprising applying the topical agent of claim 3 to the affected area of the skin.

8. A process for creating a topical agent for treating pseudofolliculitis barbae and conditioning the skin, comprising:
   a. adding Aloe Vera juice to a volume of water to form a mixture;
   b. heating said mixture of (a) to near the boiling point of said water;
   c. adding glycerine and ammonium alum to said mixture of (a) to form a second mixture;
   d. allowing said mixture of (c) to cool to near room temperature; and
   e. Adding methanol to said mixture of (d), in order to prevent precipitation in said mixture of (d).

* * * * *